(12) United States Patent
Darling et al.

(10) Patent No.: US 9,404,073 B2
(45) Date of Patent: *Aug. 2, 2016

(54) APPARATUS FOR RECYCLING OF PROTEIN WASTE AND FUEL PRODUCTION

(75) Inventors: Jonathan Scott Darling, Pender, NE (US); Don Scott Darling, Pender, NE (US)

(73) Assignee: Naturally Recycle Proteins, Johnston, IA (US)

( * ) Notice: Subject to any disclaimer, the term of this patent is extended or adjusted under 35 U.S.C. 154(b) by 236 days.

This patent is subject to a terminal disclaimer.

(21) Appl. No.: 13/563,214

(22) Filed: Jul. 31, 2012

(65) Prior Publication Data
US 2013/0029009 A1    Jan. 31, 2013

Related U.S. Application Data

(63) Continuation-in-part of application No. 12/925,359, filed on Oct. 20, 2010, now Pat. No. 9,161,554, which is a continuation of application No. 11/706,123, filed on Feb. 14, 2007, now Pat. No. 7,851,210, which is a continuation-in-part of application No. 10/607,691, filed on Jun. 30, 2003, now Pat. No. 7,226,778.

(51) Int. Cl.
| | |
|---|---|
| *A23K 1/00* | (2006.01) |
| *A01B 1/00* | (2006.01) |
| *C12P 5/00* | (2006.01) |
| *C12M 1/00* | (2006.01) |
| *A23J 1/00* | (2006.01) |
| *A23J 1/06* | (2006.01) |
| *A23J 1/10* | (2006.01) |
| *C12P 21/06* | (2006.01) |
| *C12P 5/02* | (2006.01) |

(52) U.S. Cl.
CPC .............. *C12M 21/12* (2013.01); *A23J 1/002* (2013.01); *A23J 1/06* (2013.01); *A23J 1/10* (2013.01); *A23K 10/14* (2016.05); *A23K 10/24* (2016.05); *A23K 10/26* (2016.05); *C12P 21/06* (2013.01); *C12P 5/023* (2013.01)

(58) Field of Classification Search
CPC .............. A23J 1/10; A23J 3/12; A23J 3/348
See application file for complete search history.

(56) References Cited

U.S. PATENT DOCUMENTS

| | | | | |
|---|---|---|---|---|
| 3,578,460 | A * | 5/1971 | Weeks ...................... | A23J 1/10 426/56 |
| 4,473,589 | A * | 9/1984 | Freeman et al. .................. | 426/7 |
| 6,045,070 | A * | 4/2000 | Davenport ...................... | 241/60 |
| 6,174,551 | B1 * | 1/2001 | Griffin et al. ................... | 426/53 |

* cited by examiner

*Primary Examiner* — Nathan Bowers
(74) *Attorney, Agent, or Firm* — Camille L. Urban

(57) ABSTRACT

Example embodiments provide an apparatus that is useful for recycling protein waste and producing fuel from protein waste. Waste is ground by a grinding means and digested by a enzyme digest medium composed of enzymes, preservatives, inedible egg and or a waste fluid that may include other protein sources with or without fat. The ground proteins are digested with the enzyme in recirculated digest tanks. Fat can be collected from the tank by addition of acid and separation of fat from water with a centrifuge. Alternatively the ground protein and enzyme can be fermented and gas collected from the digest tank in a pressure tank with a compressor. The protein solubles are emulsified, separated from water, and extruded before drying. Either fat or gas can be used to fuel a dryer. Example embodiments provide a highly digestable paletable food stuff from protein waste which is usable for pet, livestock, or an aquaculture diet.

15 Claims, 11 Drawing Sheets

US 9,404,073 B2

APPARATUS FOR RECYCLING OF PROTEIN WASTE AND FUEL PRODUCTION

PRIORITY STATEMENT

This is a Continuation-In-Part of U.S. application Ser. No. 12/925,359 filed on Oct. 20, 2010, now U.S. Pat. No. 9,161,554, which is a Continuation of U.S. application Ser. No. 11/706,123 filed Feb. 14, 2007 (which issued as U.S. Pat. No. 7,851,210 on Dec. 14, 2010), which is a Continuation-In-Part of U.S. application Ser. No. 10/607,691 filed Jun. 30, 2003 (which issued as U.S. Pat. No. 7,226,778 on Jun. 5, 2007), the entire contents of each application and patent being incorporated herein by reference.

BACKGROUND

1. Field

Example embodiments relate, in general, to apparatuses and processes for naturally recycling protein waste into feed and, more specifically, to apparatuses and processes for enzymatically digesting, emulsifying and drying protein waste including feathers for use in animal feed.

2. Description of the Related Art

A mass of waste is accumulated on a regular basis in such operations as poultry production facilities. Protein waste such as carcasses from animal production facilities pose problems for disposal. For example, such problems include odor and generation of bacteria in building. Carcasses are currently disposed of in many ways including land filling and burning. Natural gas production from waste materials is also known in the art and such processes typically also result in a byproduct which is used as animal feed or fertilizer. Some facilities process the protein waste to produce a component for animal feed but these plants often are not designed to provide a mostly closed system and, consequently, air, moisture, and other contaminants may enter creating an environment where microorganisms can multiply and destroy the quality or usefulness of the processed protein waste.

And, although there may be processing plants at which protein waste may be disposed and recycled, there is not an efficient way to remove the waste from the site to the processing plant in such time and condition as necessary for efficient processing. The timing of such disposal is essential to managing toxicity and odors yet it is not feasible for each animal production plant to also operate a processing plant for its protein waste.

Animal feed requires a protein component. In addition to the carcasses which can be processed for protein recovery, feathers are inexpensive and also high in protein, however, feathers are difficult for animals to digest. And, although there are processes known for forming feather meal, often these processes require steam which, if too hot, will denature the proteins in the feathers and reduce their nutritional values. It is also known that certain bacterial strains produce keritinase which is an enzyme capable of degrading feathers and that, properly employed, such degradation can result in material that can be used in animal feeds. See U.S. Pat. Nos. 4,908,220; 4,959,311.

In addition, it is known in the art to provide a means to grind swine or poultry waste and then mix it with ingredients that will facilitate fermentation of the protein waste. See U.S. Pat. No. 5,713,788. The invention disclosed therein provides a specific grinding mechanism which includes a grinding drum with a helical groove on its outer surface in which a length of chainsaw chain, teeth side out, is positioned. This invention does not include a way to re-circulate and thoroughly mix the ground protein and catalyst but, instead, depends on a metered application of catalyst to the ground protein waste as it moves past the grinder wherein the metering of the catalyst is triggered by the load on the grinder. This is deficient in that no additional mixing of the ground protein waste and catalyst is contemplated such that there is substantial risk that it will not be appropriately mixed and the catalytic action will be hampered.

What is needed is a way for the animal production facilities to efficiently and timely dispose of animal waste in such a way that is non-toxic and odor free. In addition, the system has to be affordable for the animal production facilities and the resultant recycled product must be usable. Preferably, a mostly closed system should be used to eliminate environmental contaminants and to provide avenues for recycling by-products. Finally, for any disposal of feathered animals, the system must provide a method of breaking down not only softer protein sources, but also feathers and in a manner that does not denature or destroy the food value of the proteins.

Example embodiments provide a system wherein animal protein waste is processed in such a way that a portion of the system may be mobile and can be taken from one animal production facility to another or simply positioned at one facility until it reaches capacity.

Example embodiments also provide a protein processing system which is capable of degrading feathers without destroying their food value.

Example embodiments also provide a way for many different and maybe distant animal production facilities to have routine access to a processing facility.

Example embodiments also provide a means for recycling and breaking down the animal protein wastes and to recycle by-products of the process.

Example embodiments also provide an apparatus with mixing and grinding capabilities associated with one another in a manner that results in a mostly closed system which may be an efficient process for digesting, emulsifying and drying the recycled protein waste while also providing a means for recycling other byproducts such as water and for minimizing growth of damaging micro organisms. Example embodiments also provide an apparatus for recycling animal protein that produces fuel from the digesting or fermentation of animal protein waste.

Example embodiments also provide an apparatus for animal protein recycling that produces fuel and uses the produced fuel to power portions of the apparatus.

SUMMARY

Example embodiments provide an apparatus and process for naturally recycling poultry carcasses or parts thereof for use as a nutritional supplement. The apparatus may have four modules: (1) a pH adjustable enzymatic digest medium mixing assembly, (2) a mobile grinding assembly which may be mounted on a truck trailer; (3) a digesting and emulsifying assembly which may include a heated tank and separator or alternatively a fermentation assembly; and (4) a drying system.

The enzymatic digest medium of example embodiments may include protease/keritinase, inedible egg or a waste fluid that includes protein with or without fat, water as needed, and a preservative. The amount of preservative to be added to the medium may be determined by a circuit using data from a load sensor on the grinding means to control a variable frequency drive which may control the speed of a preservative pump. The digest medium mixing assembly may be equipped with a pH probe and monitor which may trigger the addition of an acidic solution as needed to adjust a pH of the enzymatic digest.

The mobile grinding assembly may be moved from one animal production facility to another or may remain at one facility. The mobile grinding assembly of example embodiments may be mounted on a trailer and may include a holding tank for the enzymatic digest medium and a conveyor for loading carcasses into a grinder. The remainder of the grinding assembly may be a closed system. Once through the grinder, the ground carcasses or portions or parts thereof may be pumped into a storage tank with the enzymatic digest medium to produce a protein solubles mixture. This mixture may then be recirculated through a chopper pump for a few minutes to further reduce particle size of the ground protein waste and assure adequate mixing of the digest and the proteins and then pumped into a tanker truck for transport. Multiple batches of the protein solubles mixture may be generated so that the storage tanks may be filled and emptied as many times as necessary until all the waste has been disposed. Then, the mobile grinding assembly can be moved to another location or it can simply remain until it is needed again.

The protein solubles mixture created by the mobile grinding assembly may then be moved to a centralized and stationary processing plant and transferred from the tanker truck to the digesting and emulsifying assembly. An enzyme digest of the present invention in the protein solubles mixture may work best between about 100 and 130 degrees Fahrenheit while other enzyme digests disclosed work best under 125 degrees Fahrenheit. Therefore, the digesting and emulsifying assembly may heat the mixture if needed and only periodically recirculate it until the enzymatic digest has altered the protein solubles to a mostly liquid state. For embodiments that include digestion of parts that include fats, or for enzyme digest mediums that include fat content, it may be preferred to emulsify the digested protein solubles to completely disperse the fats and proteins. The digested and emulsified proteins may then pumped into a separator tank and the bottom layer of water may be drained off periodically, leaving the emulsified proteins. The water layer may then recycled back to the portion of the system where the enzymatic digest is made. The remaining emulsified proteins may then be transferred to the drying system.

In example embodiments, fats may be collected from the digest and emulsification assembly via a closeable connection and a first fats tank. Fats may be separated from the protein solubles mixture by addition of acid from an acid tank via a pump. A valve on the recirculation means may close to allow transfer of fats from the digest tank through an open closeable connection. Fats in the first fats tank may be separated from water in a centrifuge and stored in a second fats tank. The water collected may be recycled back into the digester tank.

In alternative to the digest and emulsification assembly, the apparatus may include a fermentation assembly. In the fermentation assembly the protein solubles mixture is broken-down by bacteria which produces gas. Gas may be collected by a piping and compressed by a compressor into a pressure tank. Check valves along the piping prevent backflow of gas. The compressor may be controlled by a pressure sensor on the fermentation tank.

The dryer system may use a carrier for surface absorption of moisture, extrusion, air flow, and heat to accomplish the removal of moisture. A carrier such as cereal, soybean meal, corn or wheat mids may be fed through a volumetric feeder to a mill where it may be finely ground to provide ample surface area for absorption. The carrier may then be conveyed to a mixer where it may be mixed with the emulsified proteins until a doughlike consistency is reached. At this point, the dough is fed into an extruder to remove additional moisture and to extrude dough pellet-like pieces which may then moved by oscillating belt to the drying apparatus.

The drying apparatus may include a dryer bed which, in example embodiments, may be a conveyor belt enclosed in a housing. The housing may alternate air flow direction and have heat zones for removing yet more moisture content and a cooling zone to return the pellet-like pieces to near room temperature. The pellet-like pieces may then be moved progressively through the air flow, the heat zones and the cooling zone by the conveyor. In example embodiments, the pellet-like pieces may be sized and then run over a vibrating screen to separate the non-uniform sized pieces. Finally, the appropriately and uniformly sized pellet-like pieces may be packaged.

Other objects, features, and advantages of example embodiments will be readily appreciated from the following description. The description makes reference to the accompanying drawings, which are provided for illustration of example embodiments. However, example embodiments do not represent the full scope of the invention. The subject matter which the inventor does regard as his invention is particularly pointed out and distinctly claimed in the claims at the conclusion of this specification.

DETAILED DESCRIPTION

Example embodiments provide an apparatus and process usable for, amongst other things, naturally recycling protein waste. In example embodiments, the apparatus and process for naturally recycling protein waste may include an enzymatic digest mixing assembly shown generally as 15 in FIG. 2, a mobile grinding assembly shown generally as 40 in FIGS. 3 and 4, a digesting and emulsifying assembly shown generally as 100 in FIG. 5 or a fermentation assembly shown generally as 200 in FIG. 6, and a drying system shown generally as 126 in FIGS. 7 and 8. These components may all be present on a movable platform or separated; for example, the mobile grinding assembly may be movable while the enzymatic digest mixing assembly is stationary.

Figure 9:
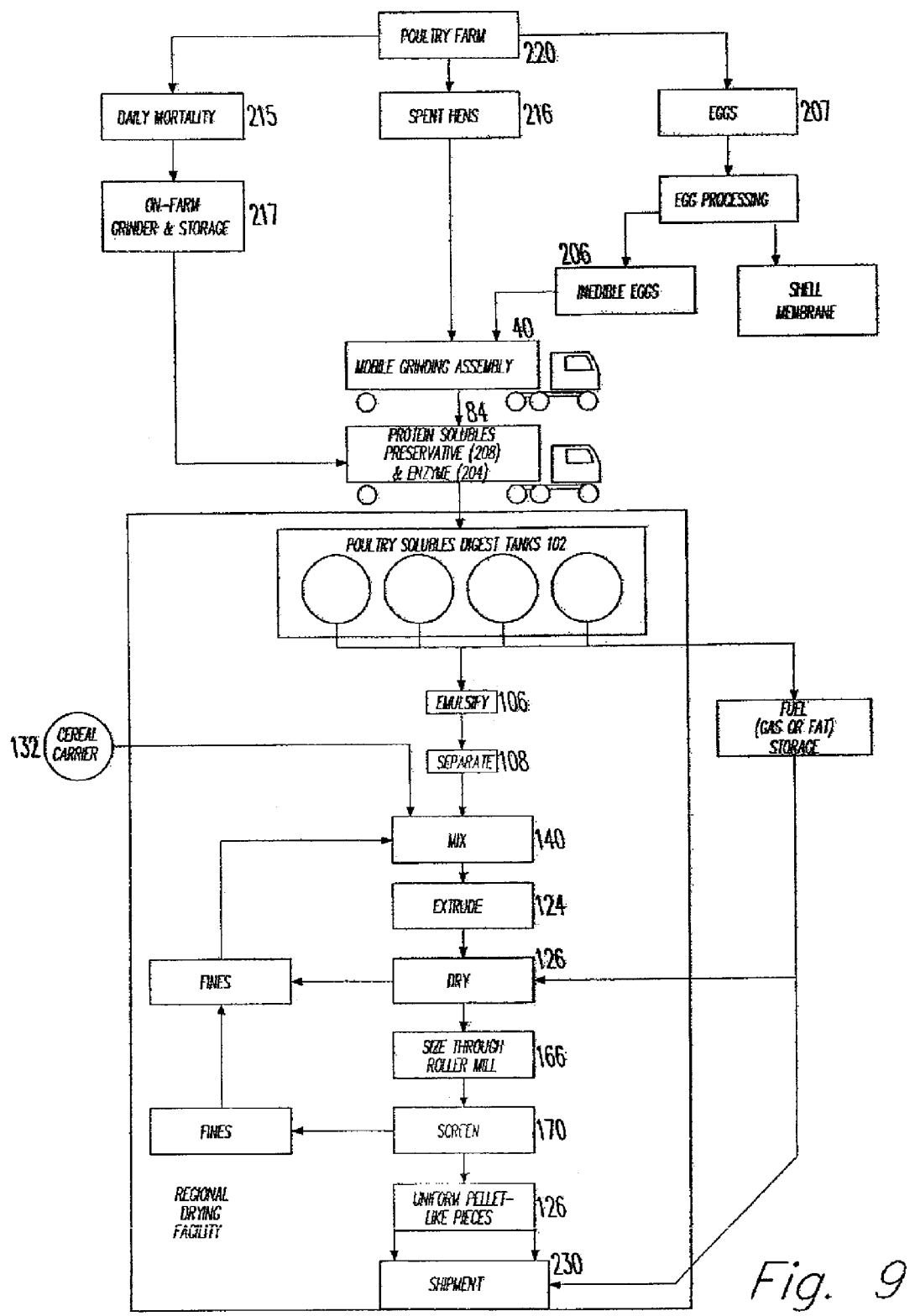
FIG. 9 is a flow diagram showing the steps for the process for natural recycling of protein waste in accordance with example embodiments.

In example embodiments, the process, as is shown in the flow chart depicted in FIG. 9, may include an enzymatic digest medium 12 of a particular pH level that may be prepared and stored until such time as it is needed. The enzymatic digest medium 12 of example embodiments may include enzymes 14, inedible egg 16, a preservative 18, and water. The enzymes 14 may include protease to break down and digest most proteins, and keritinase to aid in digestion of feathers. The preservative 18 may restrict multiplication of bacteria or microorganisms which could adversely affect the end product. Although inedible egg is a logical choice when the process is used in conjunction with poultry production, other fluid wastes such as outdated ice cream, molasses, milk by products, and others that include proteins, fat, and water or proteins without fat such as blood could be appropriately substituted.

In example embodiments, a pH of the enzymatic digest medium 12 may be adjusted by a measured addition of an acid. One such acid may be phosphoric acid, to maintain a level of pH 5 or within the range of about 4-6 or 4-8. Using phosphoric acid to effect a change in pH include the added benefit of adding phosphorous to the medium and, in turn, provides a high phosphorous product which may enhance the desirability of the additive for animal feed. Other acidic solutions may also be used. For example, lactic acid is one such reasonable alternative. In the case where lactic acid is used, the fermentation process which occurs as a natural consequence of the use of lactic acid, (in addition to digestion by enzymes) also acts to break down the protein waste and lowers the pH at the same time.

In example embodiments, protein waste 216, which may be in the form of spent hens or some portions thereof, may be ground and the enzymatic digest medium 12 and ground protein waste 216 may be thoroughly mixed and re-circulated through a chopper pump 88 to produce a protein solubles mixture 84. The protein solubles mixture 84 may be maintained at or heated to a temperature optimal for enzyme digestive action which may range between about 90 degrees Fahrenheit and about 125 degrees Fahrenheit and may be recirculated periodically until the mixture is mostly liquid. The heat created by the exothermic digestive process and the friction of recirculation in certain conditions may be enough to maintain the optimal temperature and, if not, additional heat may be provided. For example, the mixture may be recirculated for 1 hour every 12 hours for 3-4 days, however, the speed of the process may be increased if additional enzyme is used. Further, the speed is effected by the nature and content of the protein solubles mixture and may be dramatically shortened. For example, in one embodiment, digestion may be complete in as little as about 30 minutes to about 1½ hours. In example embodiments, the protein solubles mixture 84 may be strained and when the number of quills remaining in the strainer is acceptable, the digestion is complete. In example embodiments, the protein solubles mixture 84 may be emulsified to disperse fats and proteins and the protein solubles mixture 84 may be allowed to separate. A resulting water layer 125 may be drained off and recycled to be re-used for mixing enzymatic digest medium 12 and the emulsified proteins 121 may be mixed with a carrier 132. In example embodiments, the resulting water layer 125 may be drained several times before the emulsified proteins 121 are mixed with a carrier 132.

In example embodiments the carrier 132 may be delivered to a high speed mixer 140 by volumetric feeder 130. The carrier 132 may comprise a relatively high surface area to volume ratio which acts to absorb some of the moisture. Upon mixing with the emulsified proteins 121, a doughlike mixture is produced. The doughlike mixture may then be extruded into a plurality of pellet-like pieces 146 and the pellet-like pieces may be passed through a drying apparatus 126 which may use air flow, multiple heat zones, and at least one cooling zone for further removal of moisture. The pellet-like pieces may be finally sized through a mill 166 to a uniform, granular size. In example embodiments the mill 166 may be a hammer mill. The off-size pellet-like pieces may be removed and the remaining uniform, granular pellet-like pieces may be packaged. An apparatus usable to accomplish the foregoing process is described below.

Figure 1:
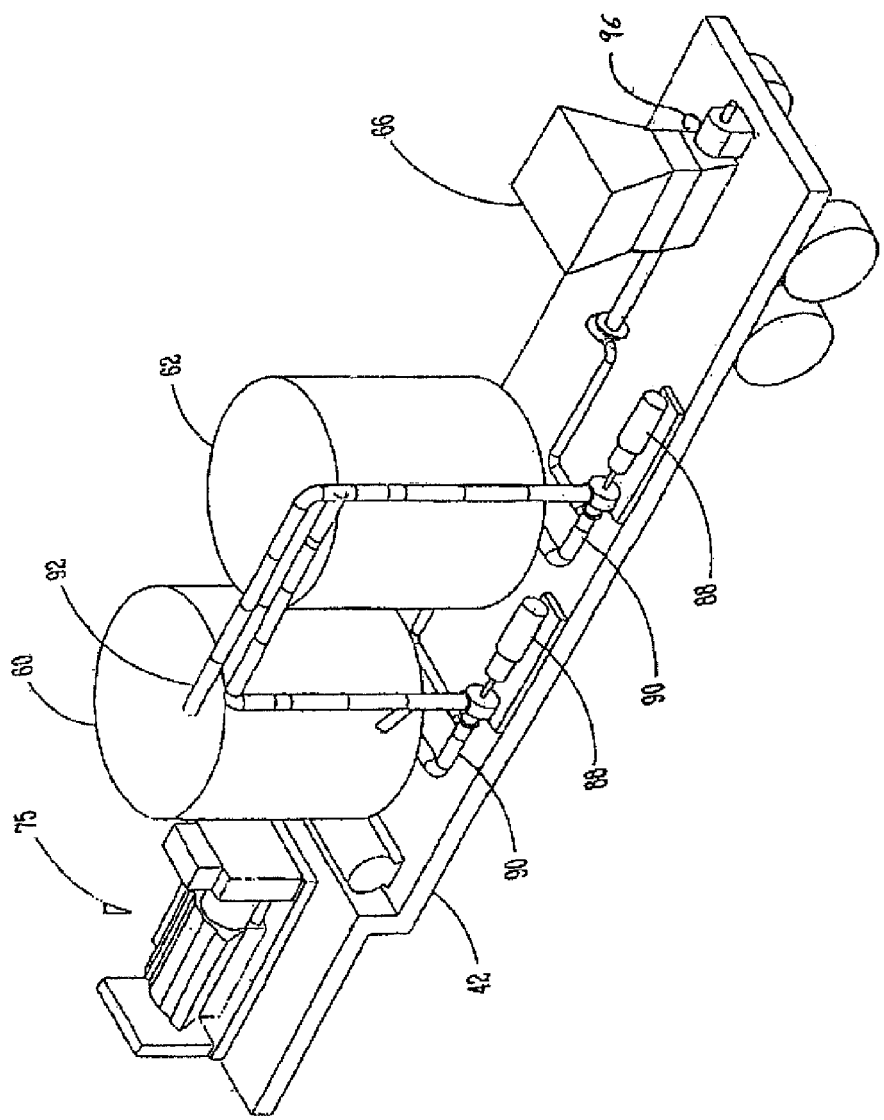
FIG. 1 is a perspective view of a mobile grinding assembly portion in accordance with example embodiments.
Figure 2:
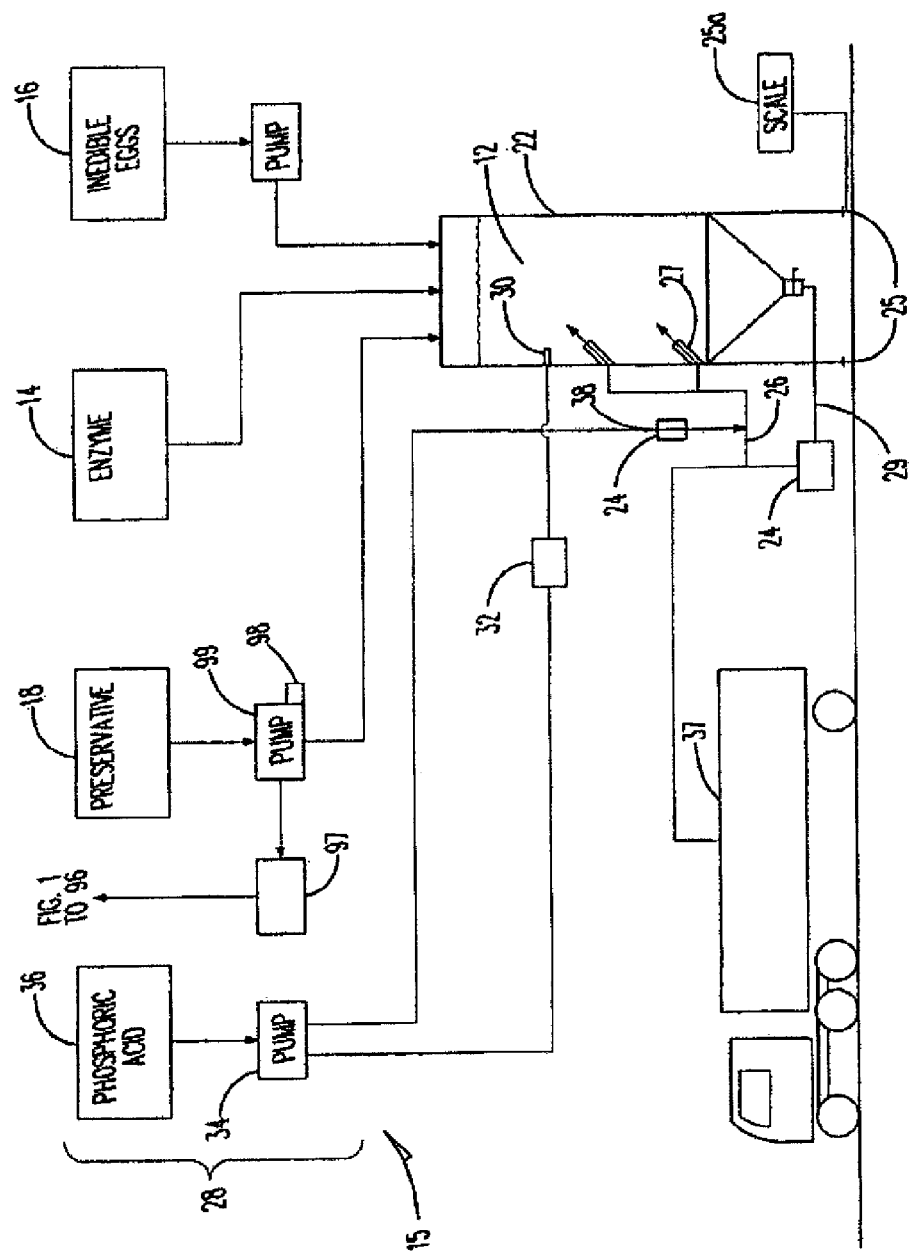
FIG. 2 is a diagram showing an enzymatic digest mixing assembly portion in accordance with example embodiments.

An example of an enzymatic digest mixing assembly 15 is shown in FIG. 2. In example embodiments, the enzymatic digest mixing assembly 15 may be used to mix enzymes 14, inedible egg 16, and a preservative 18 with water to form an enzymatic digest medium 12 of a given, predetermined, preset, or optimal pH level. The enzymatic digest mixing assembly 15 may include at least one enzymatic digest mixing tank 22, pumping means 24, a re-circulating assembly 26, and means for adjusting the pH level of the enzymatic digest medium 12 which, in example embodiments, may be a pH adjustment assembly 28. The pumping means 24 of example embodiments may comprise a first centrifugal pump and the re-circulating assembly 26 may comprises a first inductor nozzle 27 associated with the pumping means 24 and a return pipe 29 for circulating the enzymatic digest medium 12. In example embodiments, the enzymatic digest mixing assembly 15 may further include load cells 25 associated with a digital scale 25*a* and positioned such that addition of the enzymes 14, preservatives 18, and inedible egg 16 can be measured. It is also contemplated that, in addition to external measuring of the ingredients, other internal measurement options such ultrasound and light beams may be used to monitor the amounts of each ingredient as it is added.

The pH adjustment assembly 28 of example embodiments may include a pH probe 30, a pH monitor 32, and a first positive displacement pump 34 all electrically associated, and a supply of acidic solution 36 fluidly connected to the positive displacement pump 34 and to the enzymatic digest mixing tank 22 through a check valve 38. The first positive displacement pump 34 of example embodiments may include a variable speed motor. In example embodiments, the variable speed motor may be configured to pump 1-10 gallons per minute. In example embodiments, the enzymatic digest medium 12 may be formed and or placed in the mixing tank 22 and recirculated while a pH of the enzymatic digest medium 12 is monitored by the pH monitor 32. For example, the enzymatic digest medium 12 may be recirculated for at least 3-5 minutes while the pH probe 30 provides a pH level to the pH monitor 32. In example embodiments, the pH monitor 32 may compare the pH level with an optimal, preset, predetermined, or given level and send a signal to the positive displacement pump 34 to move the acidic solution 36 into the mixing tank 22 where recirculation continues. The re-circulating assembly 26 may continue to mix the enzymatic digest medium 12, the pH probe 30 may again measure the pH level, and the monitor 32 may compare the level to the optimal, preset, predetermined, or given level, and again determine whether acidic solution 36 should be added to the mixing tank 22. When the pH level reaches the optimal, preset, predetermined, or given level, the enzymatic digest medium 12 is ready to be used or stored.

A particular example of the enzymatic digest medium 12 includes, per ton, about 2½ pounds of protease and keritinase 14, about 2 pounds of preservative 18, and the remaining pounds inedible egg 16 and water. In this example, the pH was lowered to about 5 by addition of phosphoric acid 36. This pH level is optimal for this particular enzymatic digest medium, however a range from about 4-6 may be effective and the amount of enzyme may be altered according to the speed of digestion desired and the enzymes used.

Figure 3:
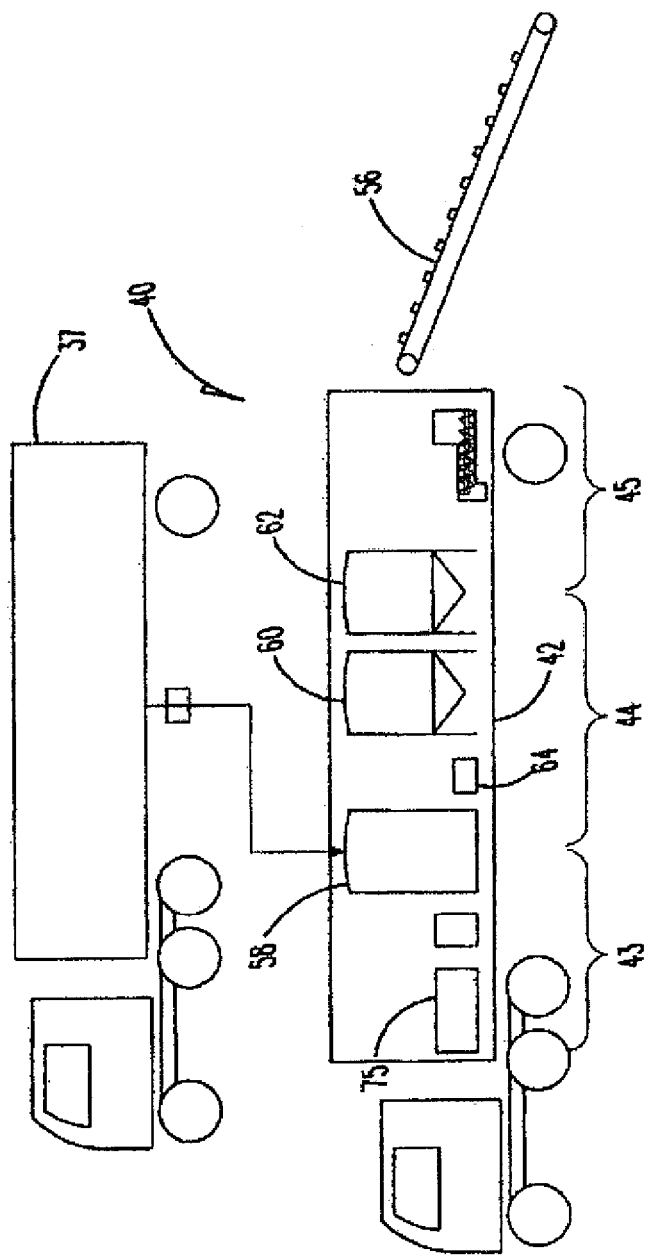
FIG. 3 is a side view of a mobile grinding assembly portion in accordance with example embodiments.
Figure 4:
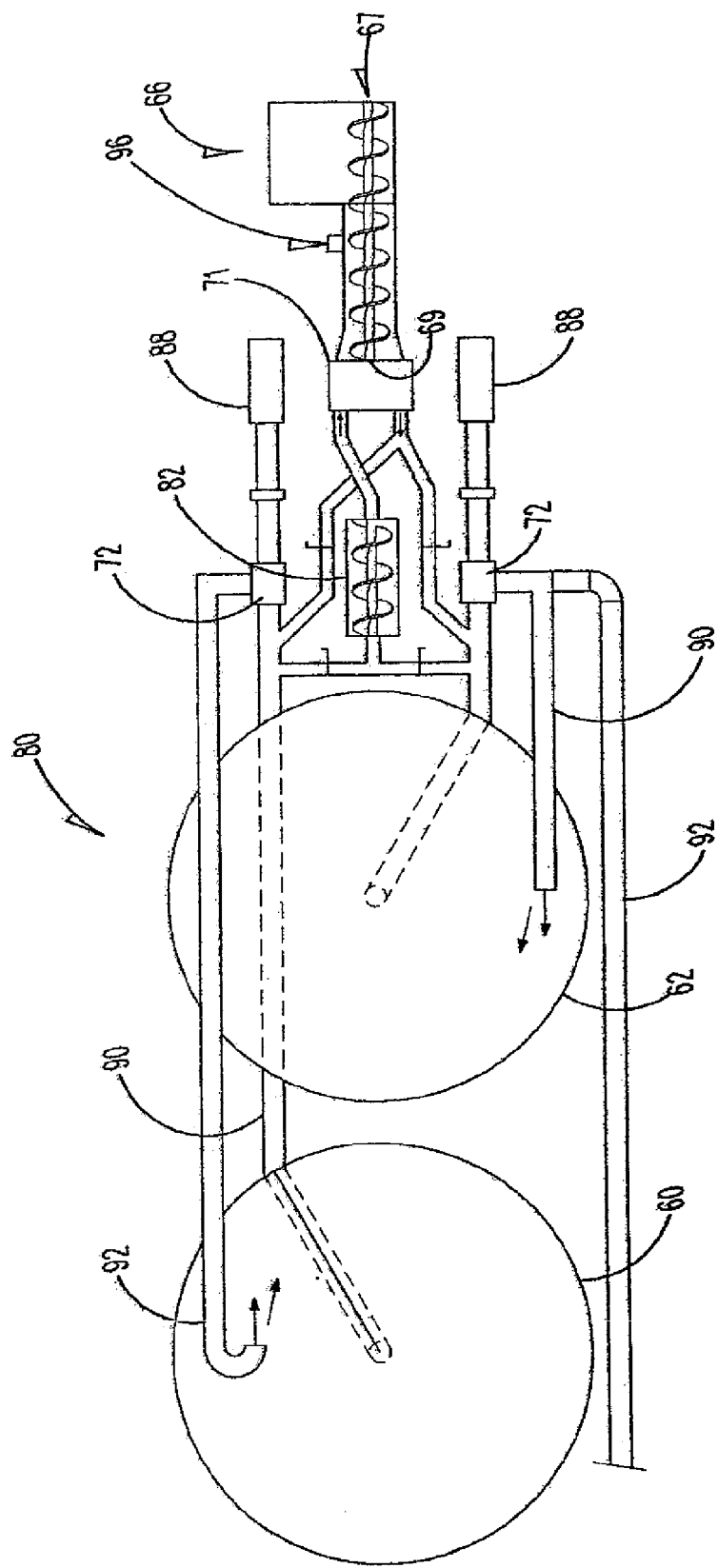
FIG. 4 is an enlarged plan view of the mobile grinding assembly of FIG. 3.

In example embodiments, once the enzymatic digest medium 12 has been prepared, it can either be stored or it can be moved via a transporting device 37, such as a tanker truck, to the mobile grinding assembly 40 where it may be mixed with ground protein waste 216. Referring now to FIGS. 3 and 4, the mobile grinding assembly 40 comprises a movable platform 42 which may include a front portion 43, a mid portion 44 and a rear portion 45, a conveyor belt 56 for moving protein waste, a holding tank 58 in which the enzymatic digest medium 12 is stored, at least one prep tank 60, 62, and a pump 64 to move the enzymatic digest medium 12 from the holding tank 58 to the at least one prep tank 60, 62, in example embodiments, the movable platform 42 may be a semi trailer. The mobile grinding assembly 40 may further comprise a grinding means 66 which may include a grinder inlet 67 positioned near the conveyor belt 56, a grinder plate 68, a grinder outlet 69, and at least one grinder knife 70, wherein the grinder outlet 69 is positioned such that output from the grinder outlet 69 may flow by closed connection 71 into a hydro pump 82 the hydro pump 82 having a lower outlet 74. A specific non-limiting example of the grinding means 66 is a Weiler Meat Grinder utilizing a 7/16" plate. However, different plate combinations may be used such as double-cut, double-knife combinations with a ¾" or ⅜" plate in this situation, one knife may be positioned on the inside of the grinder plate 68 and another on the outside of the grinder plate 68.

The grinding assembly 40 may further comprise a mixing means 80 which, in example embodiments, may comprise at least one second positive displacement pump 72, which may be fluidly connected to the at least one prep tank 60, 62 and to the hydro pump 82 of the grinding means 66 such that the enzymatic digest medium 12 can be moved to the hydro pump 82 where output from the grinder outlet 69 is mixed with the enzymatic digest medium 12 to form a protein solubles mixture 84. The enzymatic digest medium 12 may be pumped against the grinder outlet 69 and may wash ground protein waste down into the hydro pump 82. The lower outlet 74 of the hydro pump 82 is fluidly connected to a centrifugal chopper pump 88 which is further associated with the at least one prep tank 60 or 62 and a recirculation piping system 92 including an inductor nozzle 90. This arrangement provides a way to move the protein solubles mixture 84 through the chopper pump 88 and into the prep tank 60 via the inductor nozzle 90 which may be positioned to generate a circular flow in the prep tank 60. The mixture 84 may be continually recirculated through the chopper pump 88 until it is of desired consistency and thoroughly mixed. This may require several minutes.

Figure 5:
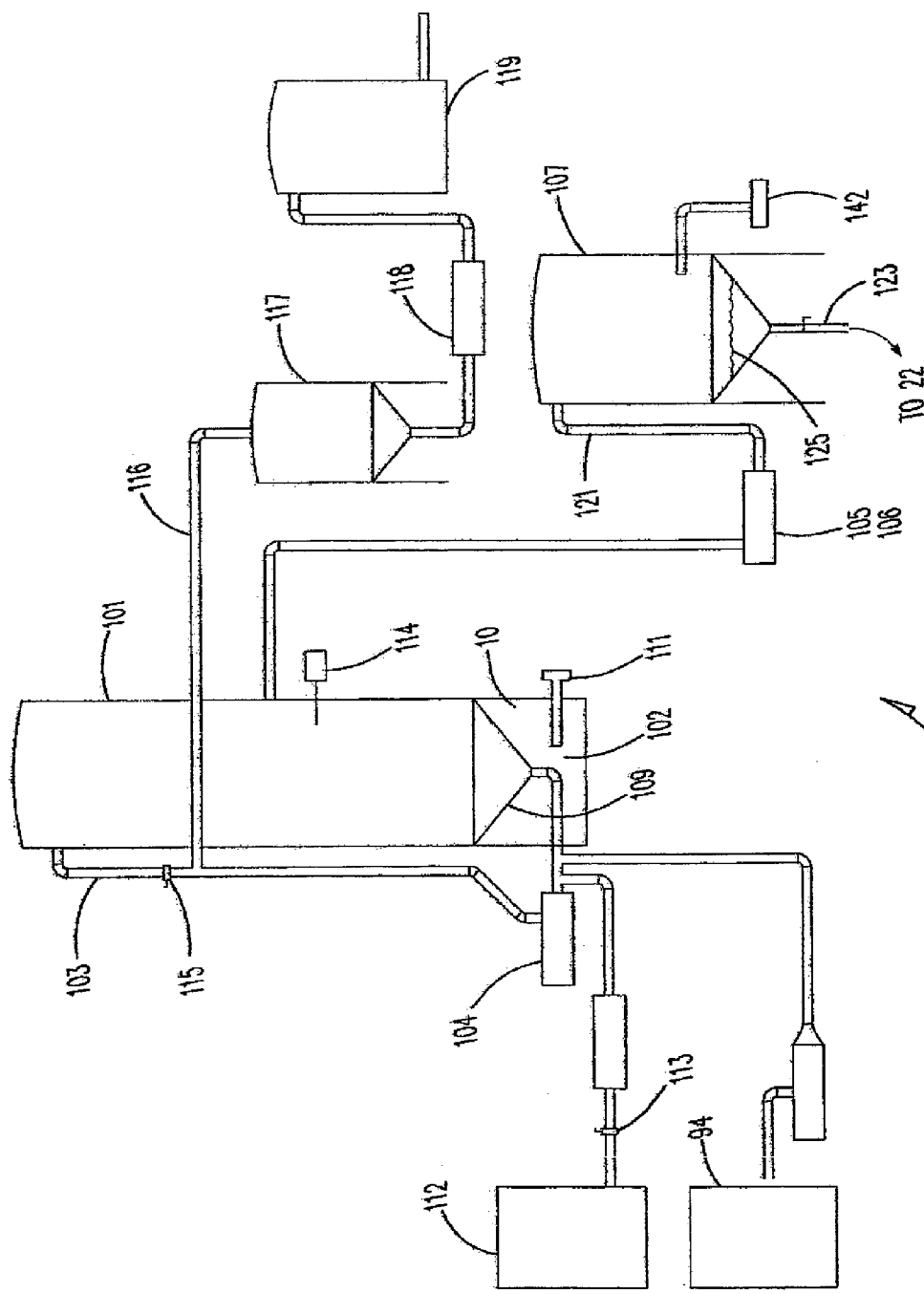
FIG. 5 is a side view of a digesting and emulsifying assembly portion in accordance with example embodiments.

The protein solubles mixture 84 may then transported to the digesting and emulsifying assembly 100, an example of which is shown in FIG. 5, either via pumping it directly or by pumping it first to a tanker truck 94 and then to the assembly 100. The mobile grinding assembly 40 may be a closed system wherein the grinder inlet 67 is the only input open to the environment.

Where more than one prep tank 60, 62 is present, one prep tank 60 may be recirculated or unloaded while another is being filled and recirculated. In this example embodiment, a separate chopper pump may be associated with each prep tank.

In example embodiments, the front portion 43 of the movable platform 42 may be occupied by a power source 75, for example, a generator, the mid portion 44 of the movable platform 42 may be occupied by the holding tank 58 and prep tanks 60, 62, and the rear portion 45 may be occupied by the grinding means 66. The conveyor belt 56 may be associated with or occupy the rear portion 45. In example embodiments, the at least one prep tank 60, 62 may be a cone-bottomed tank.

The apparatus of example embodiments may further include an electronic load sensor 96, a programmable logical computer circuit 97, a variable frequency drive 98, and a preservatives pump 99 to deliver preservative 18 to the enzymatic digest medium 12. The load sensor 96 may be located on the grinding means 66 to sense a load of the grinding means 66. The variable frequency drive 98 controls the preservatives pump 99. The load sensor 96 and variable frequency drive 98 may be connected to the programmable logical computer circuit 97. The programmable logical computer circuit 97 may be programmed with a program to determine the amount of preservative to pump based on a load.

In example embodiments, a relationship may be established between the amperage load on the grinding means 66 and the desired revolutions per minute to run the preservatives pump 99. The following program is usable in example embodiments:

| Grinder Amp | Load | Preservative Pump RPM |
| --- | --- | --- |
| 40 amps | no load | 0 RPM |
| 50 amps | 25% load | 437 RPM |
| 60 amps | 50% load | 875 RPM |
| 70 amps | 75% load | 1300 RPM |
| 80 amps | Full load | 1800 RPM |

Figure 6:
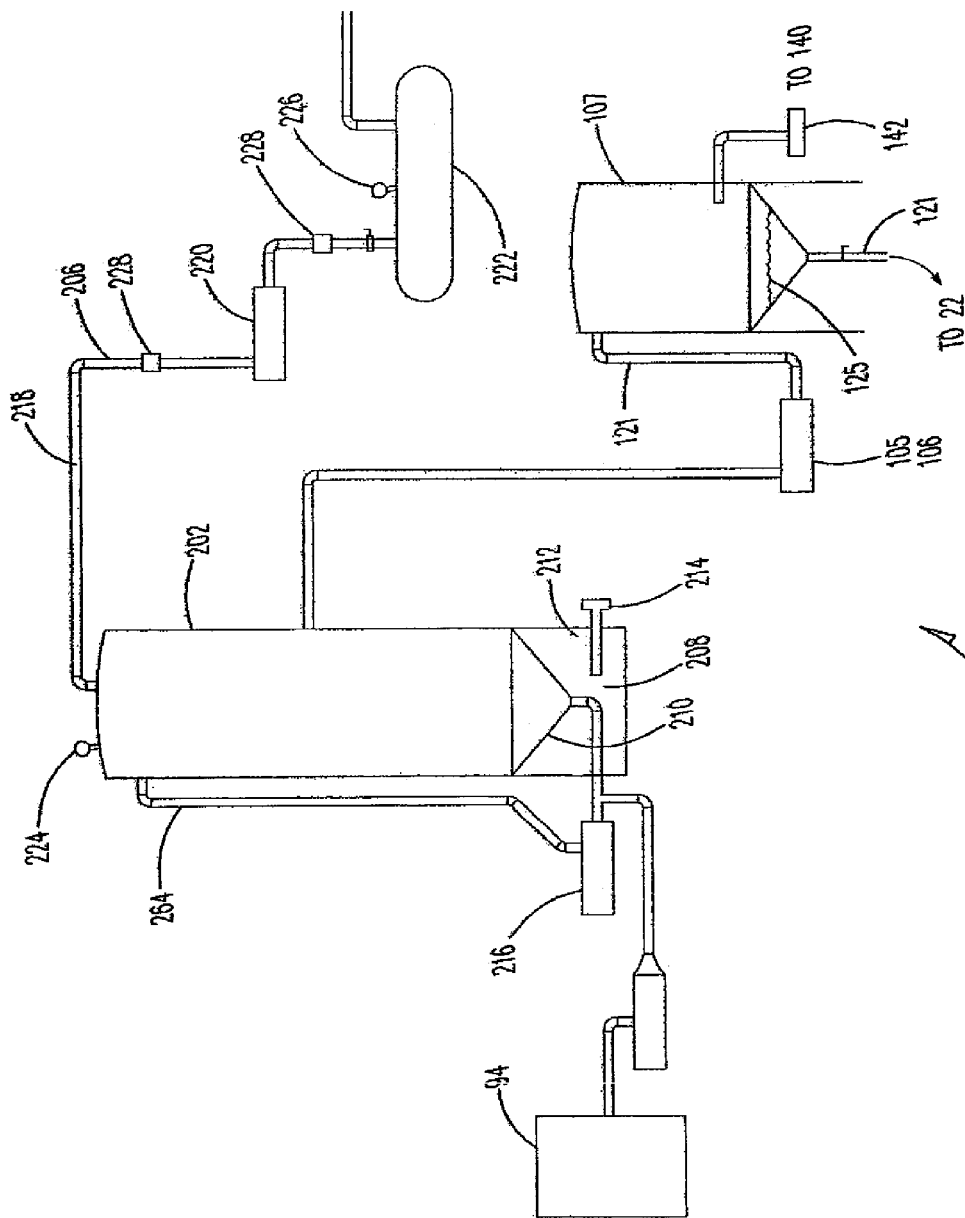
FIG. 6 is a side view of a fermentation assembly portion in accordance with example embodiments.

The digesting and emulsifying assembly 100 of example embodiments may be stationary or mobile or some portions may be mobile, while others are stationary. A non-limiting example of the digesting and emulsifying assembly 100 is shown in FIGS. 5 and 6. As shown in FIGS. 5 and 6, the digesting and emulsifying assembly 100 may include a digester tank 101 for digesting the protein solubles mixture 84, a means 102 for heating the mixture 84, a means 103 for recirculating the mixture 84 for periodic mixing, a means 107 for collecting fats from the digester tank 101, and an emulsifier 105. In example embodiments, the means 103 for recirculating the mixture 84 may include a centrifugal pump 104. The emulsifier 105 may be fluidly connected to a pump 106, the digester tank 101, and a separator tank 108.

In example embodiments, the digester tank 101 may be a non-pressure tank with a cone bottom 109 enclosed within a housing 110. The heating means 102 of example embodiments may include a heating element 111 and water (not shown) enclosed in the housing 110. The housing 110 of example embodiments may be a vented water jacket. The heating element 111 of example embodiments may heat the water in the housing to about 120° F. and in turn may warm the protein solubles mixture 84 from about 90° F. to about 110° F. The protein solubles mixtures 84 may be recirculated while it digests. In certain conditions friction from circulation and the exothermic digestion may provide heat sufficient to maintain the digest medium at an optimal temperature and reduce or negate the need for additional heat.

The fat collection means 107 of example embodiments may include an acid storage tank 112, a positive displacement pump 113, the centrifugal pump 104, a first fats storage tank 117, a centrifuge 118, and a second fats storage tank 119. After digestion of the protein solubles mixture 84 in the digest tank 101, the fat (not shown) may be separated from the protein solubles 84 by recirculating the protein solubles 84 with acid (not shown). In example embodiments, acid may be stored in the acid storage tank 112 and pumped into recirculation means 103 by the positive displacement pump 113 while the protein solubles 84 are recirculated. Alternatively, the acid could be pumped solely by the centrifugal pump 104. A pH probe 114 in the digest tank 101 may control the pump 113 and/or the centrifugal pump 104 to stop the pumps at a desired pH level.

Because acid may be introduced into the protein solubles 84, the pH of the protein solubles 84 may drop causing fat (not shown) to settle out of the digest tank 101. The settled fat may be pumped out of the digester tank 101 using the centrifugal pump 104. The recirculation means 103 includes a recirculation valve 115 and a closable connection 116 connecting the digest tank 101 to the first fat storage tank 117. During recirculation, the recirculation valve 115 is open and the closeable connection 116 is closed. During collection of fat the recirculation valve 115 is closed and the closeable connection 116 is open. In example embodiments the centrifugal pump 104 may stop pumping fat when all of the fat in the digester tank 101 has been removed as confirmed by visual operation.

The centrifuge 118 may be fluidly connected to the first storage tank 117 and the second fat storage tank 119. The centrifuge 118 may act to pump the fat from the first storage tank 117 and separate water from fat. The separated water (not shown) may be recirculated back into the protein solubles mixture 84 and water may be recycled in example embodiments. Separated fats may be stored in the second storage tank 119. The stored fats may be used as a fuel source for the drying system 120 or for other purposes.

After digestion and removal of fat, the protein soluble mixture 84 may be pumped into the emulsifier 105 for further removal of fats. Emulsification produces emulsified proteins 121 which may be transferred to a separator tank 108. The separator tank 108 may have a closeable opening 123 in fluid connection with the enzymatic digest mixing tank 22. A water layer 125 may form in the separator tank 108 and the water layer 125 may be drained for use in mixing additional digest medium 12.

Figure 7:
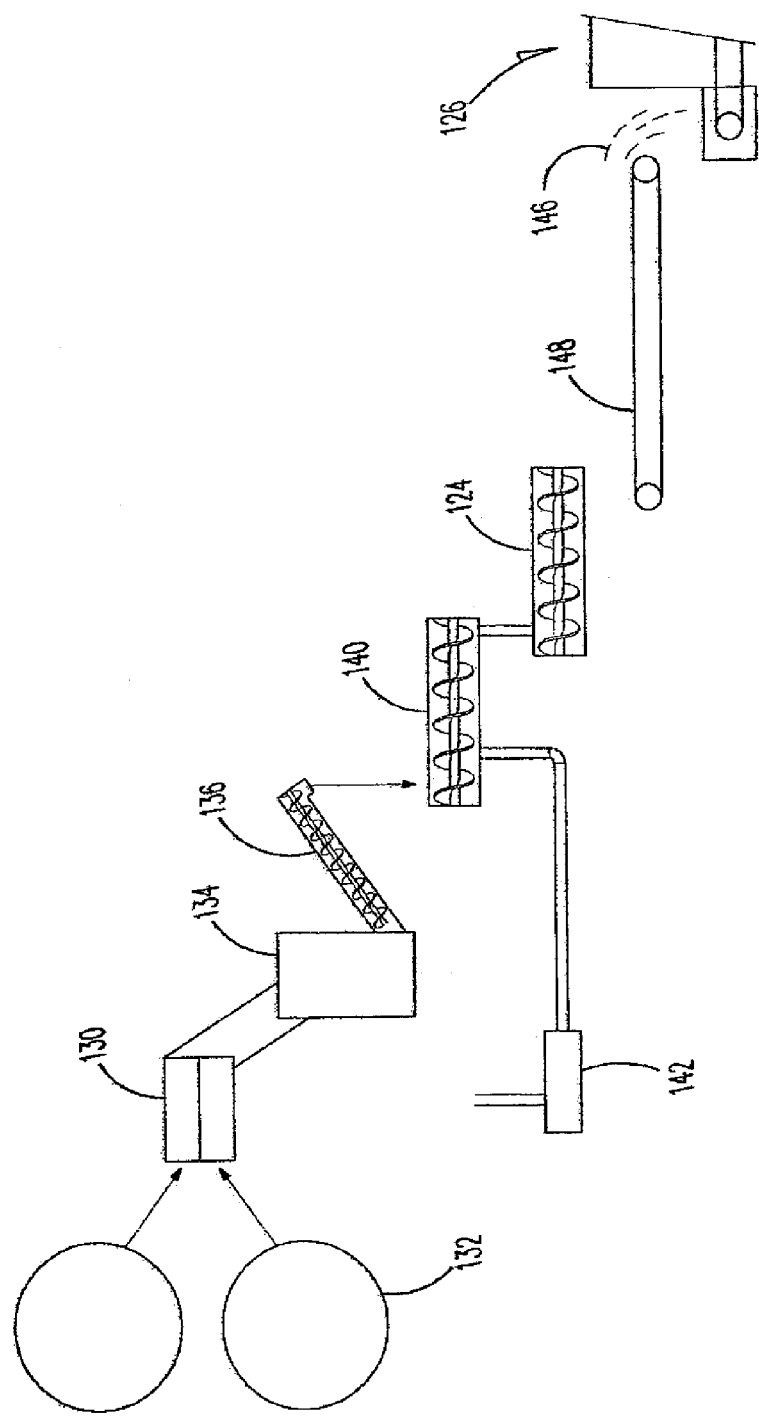
FIG. 7 is a block diagram showing the components of a dough mixing apparatus and an extruder of a drying system portion in accordance with example embodiments.
Figure 8:
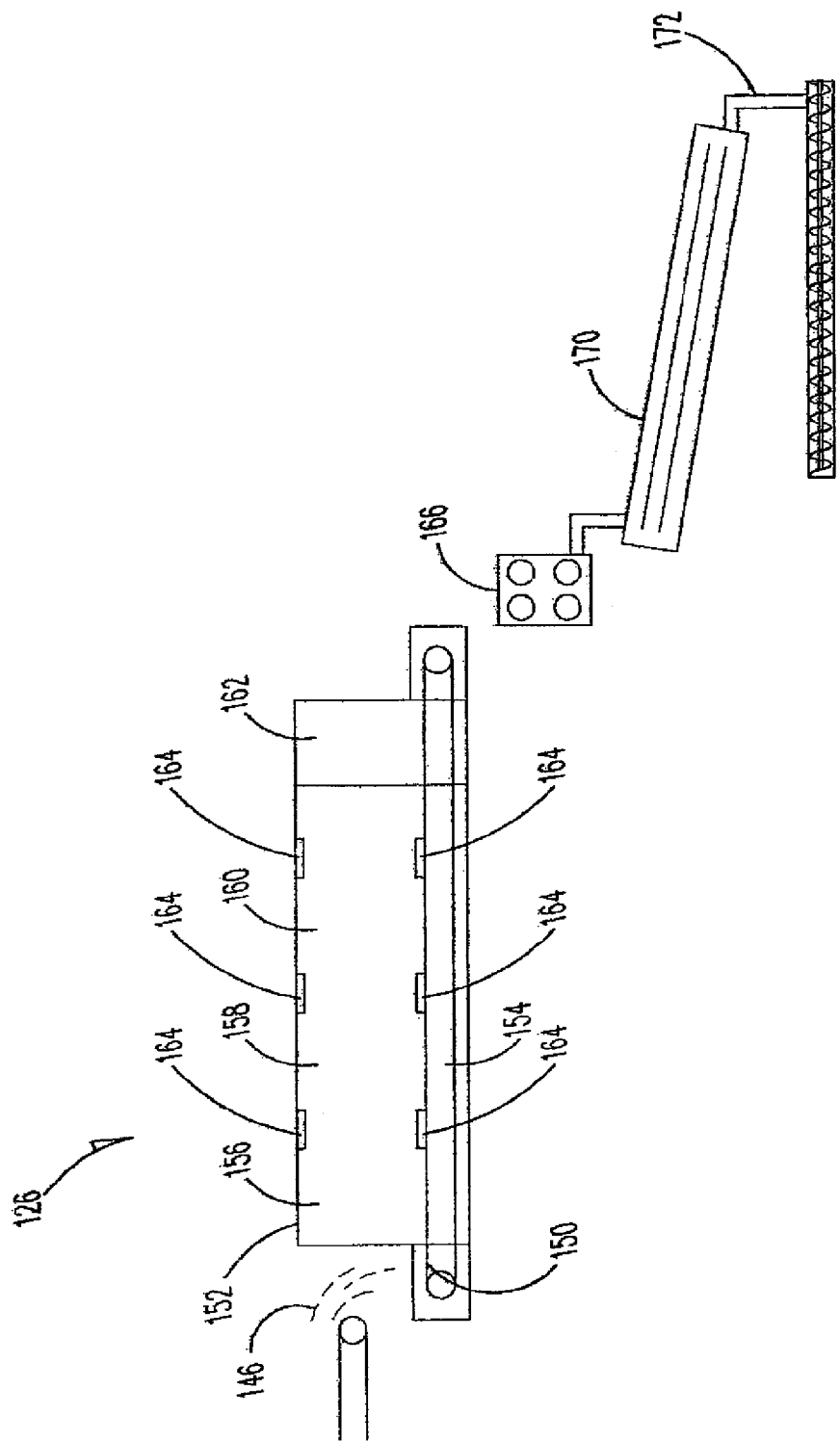
FIG. 8 is a block diagram of a drying apparatus of the drying system portion in accordance with example embodiments.

Referring to FIGS. 7 and 8, the emulsified proteins 121 may be moved to the drying system 120 which may include a dough mixing apparatus 122, an extruder 124 and a drying apparatus 126. An example of the dough mixing apparatus 122 is shown in FIG. 7. As shown in FIG. 7, the dough mixing apparatus 122 may comprise a volumetric feeder 130 for measuring an absorbing carrier 132 which may be mixed with the emulsified proteins 121. In example embodiments, the dough mixing apparatus 122 may be positioned over a mill 134 for finely grinding the absorbing carrier 132. The mill 134 may, for example, be a high speed hammer mill or disc mill. The dough mixing apparatus may further include a second conveyor belt 136 which may move the absorbing carrier 132 from the mill 134 to a high speed continuous mixer 140. A third positive displacement pump 142 may be associated with the separator tank 108 and may move the emulsified proteins 121 to the high speed mixer 140 where it may be mixed with the absorbing carrier 132 to produce a doughlike mixture. In example embodiments, the absorbing carrier 132 may be a substance with characteristics like wheat mids, soybean meal, corn, or a previously dried material made for such purpose and the third positive displacement pump 142 may be of the variable speed variety.

In example embodiments, the doughlike mixture may be moved to the extruder 124 which may pressure-force moisture out and produce a plurality of pellet-like pieces 146. In example embodiments the pellet-like pieces may have a thickness of about 3/16" and of random length. The pellet-like pieces 146 may be extruded onto an oscillating belt 148 which may distribute the pellet-like pieces 146 evenly and connect the extruder 124 to the drying apparatus 126. Additional moisture may be removed by the drying apparatus 126 using heat and air movement. An example of the drying apparatus 126, as shown best in FIG. 8, may comprise a dryer bed 150 positioned to receive the pellet-like pieces 146 from the oscillating belt 148, a housing 152 through which a dryer bed conveyor belt 154 may move and convey the pellet-like pieces 146 and which may include at least one heating zone 156, 158, 160, at least one cooling zone 162, and means to direct airflow 164. The mill 166 may receive the pellet-like pieces 146 after they emerge from the housing 152 and size the plurality of pellet-like pieces 146 to a uniform size. A vibrating screen 170 may be used to remove any of the plurality of the pellet-like pieces 146 which are of a non-uniform size. In example embodiments, the means to direct airflow 164 may comprise fans positioned to alternate the flow of air to provide uniformity in drying. In example embodiments, the heat zones 156, 158, 160 may provide temperatures of 300, 275, and 250 Fahrenheit, in this order, such that the maximum temperature of the plurality of pellet-like pieces does not exceed 250 Fahrenheit. If the heat of the pellet-like pieces 146 exceeds this level their taste may be too bitter and the amino acids may be degraded. The cool zone 162 may return the pellet-like pieces 146 to within about 10 degrees of ambient temperature. Vents may return the heated air from the cool zone 162 to the heat zones.

The protein solubles mixture 84 may alternatively be digested through fermentation. In this example embodiment, the pH of the enzymatic digest medium 12 may be adjusted using lactic acid. The fermentation itself replaces the enzymatic digest and a fermentation assembly 200 replaces the digest and emulsification assembly 100. The fermentation assembly 200 may include a non-vented low pressure tank 202, a means 264 for recirculating protein solubles 84, and a means 206 for collecting gas.

In example embodiments, the fermentation tank 202 may have a means 208 for heating the mixture 84 comprising a cone bottom 210 surrounded by a housing 212 filled with water (not shown) and heated by a heating element 214. The heated water in turn heats the protein solubles mixture 84 and microorganisms (not shown) within the tank 202. The microorganisms in the tank 202 may be bacteria that produce methane gas. In example embodiments, the recirculation means 264 may include a centrifugal pump 216 that may recirculate the contents of the tank 202. In example embodiments, the gas collection means 206 may comprise piping 218 in fluid connection with the tank 202, a compressor 220, and a pressure tank 222. During recirculation, the bacteria may produce gas (not shown) and may increase pressure in the tank 202. In example embodiments, the tank 202 may include a pressure sensor 224 to monitor pressure in the tank 202. At the appropriate pressure, the pressure sensor 224 may activate the compressor 220 which may compress the gas for storage in the pressure tank 222. As a safety measure, the pressure tank 222 may include a pressure guage 226. To prevent backflow of gas, the piping 218 may include check valves 228 located before and after the compressor 220. The stored methane gas may be used as a fuel source for the dryer system 120 or for other purposes. After digestion and collection of gas, the protein soluble mixture 84 may be pumped into the emulsifier 105 for further removal of fats consistent with the earlier described example digest and emulsification assembly 100.

Example embodiments provide a process to treat animal byproducts or only portions of animal carcasses. For example, some embodiments provide a method to treat blood and feathers which are waste products of a poultry processing plant, and to treat this mixture on site at least to the degree necessary to avoid bacterial contamination and reduce other negative effects of a rendering plant. The method reduces or minimizes problems associated with odor and bacteria, such as *salmonella* and *E. coli*. Embodiments also provide a method of treating byproducts in a manner that is sanitary. The various embodiments will provide a product that is a high protein material. One use of the high protein material is as an additive to existing animal foods and/or as a new ingredient for animal foods. For example, the high protein material may be added to a feed additive.

In example embodiments, blood and feathers, and optionally offal, necks, backs and/or wings, may be collected on site of a rendering plant or a slaughter plant. These products may be collected into stationary or mobile tanks. In example embodiments, the blood may be combined with enzymes and preservatives to form an enzymatic digest medium; the enzymatic digest medium, in turn, may be combined with the feathers, and optionally offal and/or other parts remaining. Preferably the feathers are ground prior to addition to the enzymatic digest medium which will decrease the time necessary to achieve the degree of digestion required. The enzymes in the enzymatic digest medium will liquefy substantially all of the feathers (and offal, if present) and the progress of the digestion can be monitored by checking the level of quills remaining. Once the number of quills or quill parts is at the desired level, the digestion process may be allowed to end by removing the heat supply, or adjusting the pH or by other known means. The digested mixture may be stored for a relatively long period of time. It may be used in its liquid state or dried using heat, and thereafter milled in the presence of cereal that operates as a carrier or combined with another material prior to or during drying.

Where offal is included in the digest medium, or added to the digest medium at a later time, fat will be present. The fat may be separated as described herein, and the remaining portion be emulsified, with drying of the material to follow.

In example embodiments, the processes may occur in a mobile or a stationary system. The digest equipment may include a tank for producing the digest medium and another tank for the actual digestion process. The second tank may be equipped with a means to stir the enzymatic digest and the animal byproducts and a means to pump the material out when finished. The first and second tanks may be configured with a heating system to heat the mixture of the animal byproducts and the enzymatic digest medium while the mixture is mixing.

Figure 10:
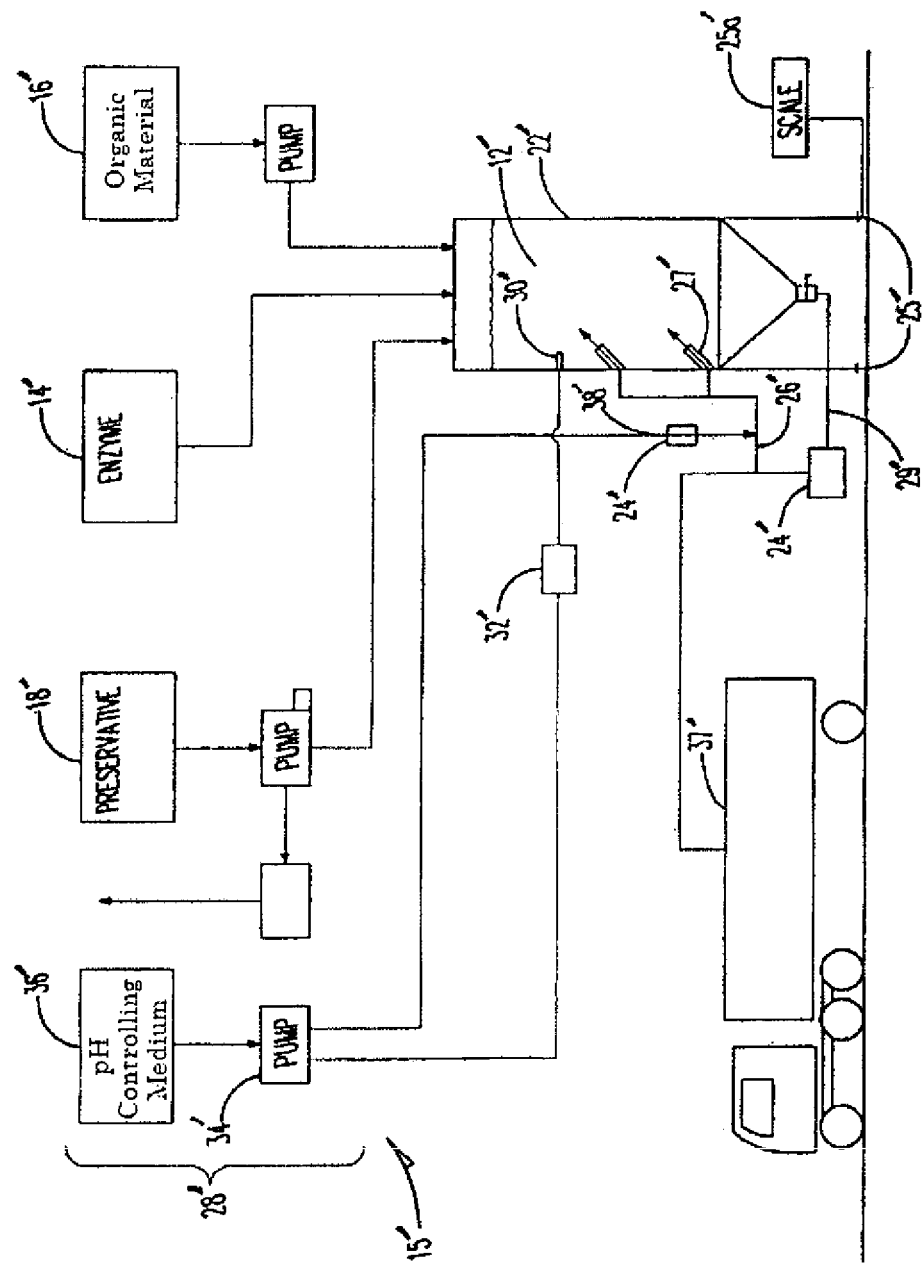
FIG. 10 is a diagram showing an enzymatic digest mixing assembly portion in accordance with example embodiments.

FIG. 10 is a view of an enzymatic digest mixing assembly 15' in accordance with example embodiments. In example embodiments, the enzymatic digest mixing assembly 15' of FIG. 10 is similar to the example enzymatic digest mixing assembly 15 of FIG. 2. For example, as shown in FIG. 10, the enzymatic digest mixing assembly 15' may include an enzymatic digest tank 22' which may be configured to receive a preservative 18', at least one enzyme 14', an organic material 16', and water. In example embodiments, the preservative 18', the at least one enzyme 14', the organic material 16', and the water may be mixed in the enzymatic digest tank 22' to form an enzyme digest medium 12'. In example embodiments, a moisture content of the enzyme digest medium 12' may be about 65% or greater to render the enzyme digest medium 12' usable for digesting animal byproducts (for example, feathers, to be explained later).

In example embodiments the organic material 16' may be blood, for example, avian blood such as chicken or turkey blood. The at least one enzyme 14' may be a protease, a lipase, a keratinase, an amylase, or a combination thereof. Thus, the at least one enzyme 14' may be capable of breaking down proteins or fats that may be present in the enzyme digest medium 12' or proteins or fats that may be combined with the enzyme digest medium 12'. For example, the enzymatic digest medium 12' may be combined with feathers either during the production of the enzymatic digest medium 12' or added to the enzymatic digest medium 12' at a later time.

In example embodiments, the preservative 18' may be a preservative or an agent that prevents or reduces microbial growth. For example, non-limiting examples of the preservative 18' are sodium bisulfate, meta-bisulfate, a reducing agent, potassium sorbate, sodium sulfate, phosphoric acid, and hydrochloric acid. The proper selection of a preservative or a combination of preservatives depends on the materials to be digested and the enzyme digest itself. In example embodiments, the enzyme digest medium 12' may be stably stored for a long period of time due to the presence of a preservative 18'. For example, the enzymatic digest medium 12' may be stored for several months prior to its use.

In example embodiments, the enzymatic digest mixing tank 22' may be further configured to receive a pH controlling medium 36'. In example embodiments, the pH controlling medium 36' may be a basic medium or an acidic medium. For example, non-limiting examples of the pH controlling medium 36' may be sodium hydroxide or phosphoric acid. The addition of the pH controlling medium 36' may be helpful in regulating a pH of the enzyme digest medium 12'. In example embodiments, the pH controlling medium 36' may be added to the enzymatic digest mixing tank 22' by a pH adjustment assembly 28' which may be comprised of a pump 34', a pH monitor 32', and a pH probe 30'. In example embodiments, the pH probe 30' may be exposed on an inside of the enzymatic digest tank 22' and thus may be exposed to the enzymatic digest medium 22'.

In example embodiments, the pH probe 30', the pH monitor 32', and the first positive displacement pump 34' may be electrically associated, and a supply of pH controlling medium 36' may be fluidly connected to the positive displacement pump 34' and to the enzymatic digest mixing tank 22' through a check valve 38'.

The first positive displacement pump 34' of example embodiments may include a variable speed motor. In example embodiments, the variable speed motor may be configured to pump 1-10 gallons per minute. In example embodiments, the enzymatic digest medium 12' may be formed or placed in the mixing tank 22' and recirculated while a pH of the enzymatic digest medium 12' is monitored by the pH monitor 32'. For example, the enzymatic digest medium 12' may be recirculated for at least 3-5 minutes while the pH probe 30' provides a pH level to the pH monitor 32'. In example embodiments, the pH monitor 32' may compare the pH level of the enzymatic digest medium with a predetermined, preset, or optimal pH level and send a signal to the positive displacement pump 34' to move the pH controlling medium 36' into the mixing tank 22' where recirculation continues. The re-circulating assembly 26' may continue to mix the enzymatic digest medium 12', the pH probe 30' may again measure the pH level, and the monitor 32' may compare the pH level to the predetermined, preset, or optimal pH level and again determine whether the pH controlling medium 36' should be added to the mixing tank 22. When the pH level reaches the predetermined, preset, or optimal pH level, the enzymatic digest medium 12' is ready to be used or stored.

In example embodiments, the enzymatic digest mixing assembly 15' may be used to mix the at least one enzyme 14', the preservative or preservatives 18', the organic material 16', and water. The enzymatic digest mixing assembly 15' may also be usable for mixing the pH controlling medium 36' with the enzymes 14', the preservative 18', the organic material 16', and the water to form the enzymatic digest medium 12' of a predetermined, preset, or optimal pH level. For example, the enzymatic digest mixing assembly 15' may produce an enzymatic digest medium 12' having a pH of about 7. In example embodiments, the enzymatic digest mixing assembly 15' may include a pump 24' and a re-circulating assembly 26'. The pump 24' of example embodiments may comprise a first centrifugal pump and the re-circulating assembly 26' may comprise a first inductor nozzle 27' associated with the pump 24' and a return pipe 29' for circulating the enzymatic digest medium 12'. In example embodiments, the pump 24' may alternatively be another type of pump, for example, a chopper pump.

In example embodiments, the enzymatic digest mixing assembly 15' may further include load cells 25' associated with a digital scale 25a' and positioned such that addition of the at least one enzyme 14', preservatives 18', and organic material 16' can be measured. It is also contemplated that, in addition to external measuring of the ingredients, other internal measurement options such ultrasound and light beams may be used to monitor the amounts of each ingredient as it is added.

In example embodiments, the enzymatic digest mixing assembly 15' may be a stationary structure. For example, the enzymatic digest mixing assembly 15' may be a stationary structure used at a slaughter house. In this case, the organic material 16' may be blood, for example, avian blood, and the blood may be transferred to the mixing tank 22'. In this particular nonlimiting example embodiment, the avian blood produced as part of a slaughter operation may be mixed with the at least one enzyme 14' and the preservative or preservatives 18 in the enzymatic digest mixing tank 22'. Due to the presence of the preservative 18, the mixture of the blood, the enzymes 14', and the preservative 18' may be stored for a relatively long period of time. Thus, the enzymatic digest medium 12' may be stored in the mixing tank 22' for an indefinite period of time or may be pumped to a holding tank for an indefinite period of time. In example embodiments, a pH of the enzymatic digest medium 12' may be controlled via the pH adjustment assembly 28'. For example, the pH of the enzymatic digest medium 12' may be controlled to be around 7.

In example embodiments, the mixing tank 22' may be transportable and thus may be moved from one facility to another facility. In the alternative, the enzymatic digest medium 12' may be pumped from the mixing tank 22' to a holding tank which may be loaded on a truck. Example embodiments, however, are not limited thereto. For example, the entire enzymatic digest mixing assembly 15' may be truck mounted. Thus, the entire enzymatic digest mixing assembly 15' may be mobile.

In example embodiments, the enzymatic digest medium 12' may be usable for digesting proteins, for example, proteins from feathers. For example, an avian slaughtering operation may produce by products such as blood, offal, and feathers. The blood may be used as the organic material 16' in producing the enzymatic digest medium 12'. At least one of the feathers and offal may be collected, ground, and added to the enzymatic digest medium 12' either during a production of the enzymatic digest medium 12' or afterwards.

Figure 11:
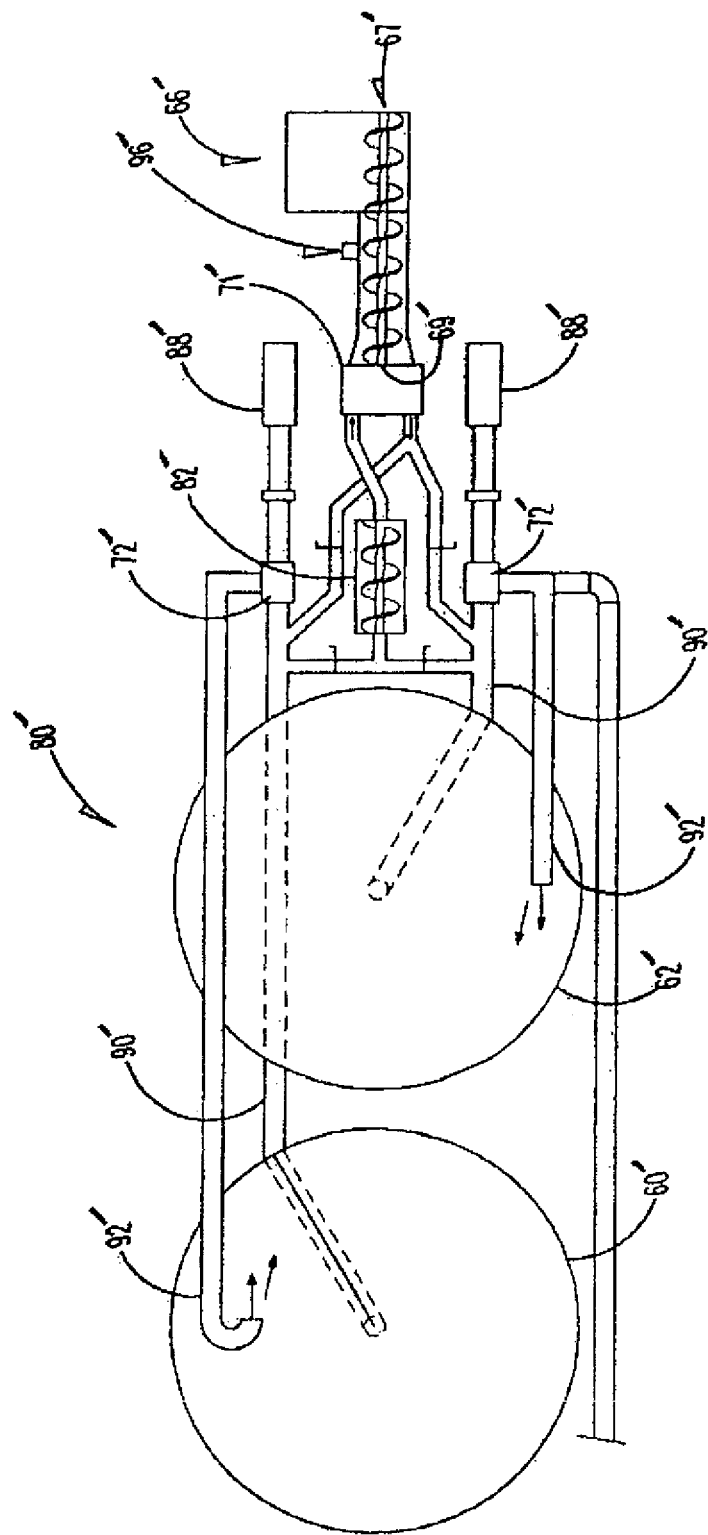
FIG. 11 is a plan view of a mixing device and a grinding assembly in accordance with example embodiments.

FIG. 11 is a view of a mixing system 80' that may be usable for mixing animal products, for example, feathers and/or offal, with the enzymatic digest medium 12'. The mixing system 80' may be substantially the same as the mixing system 80 illustrated in FIG. 4. For example, the mixing system 80' may comprise at least one second positive displacement pump 72', which may be fluidly connected to the at least one prep tank 60', 62' and to the hydro pump 82' such that the enzymatic digest medium 12' can be moved to a hydro pump 82' where output from the grinder outlet 69' is mixed with the enzymatic digest medium 12' to form a protein solubles mixture 84'. The enzymatic digest medium 12' may be pumped against the grinder outlet 69' and may wash ground protein waste down into the hydro pump 82'. The lower outlet 74' of the hydro pump 82' may be fluidly connected to a centrifugal chopper pump 88' which may be further associated with the at least one prep tank 60', 62' and a recirculation piping system 92' including an inductor nozzle 90'. This arrangement provides a way to move the protein solubles mixture 84' through a chopper pump 88' and into the at least one prep tank 60', 62' via the inductor nozzle 90'. The system may be arranged to generate a circular flow in the at least one prep tank 60', 62'. The mixture 84' may be continually recirculated through the chopper pump 88' until it is of desired consistency and thoroughly mixed. This may require several minutes, for example, sixty (60) minutes.

In example embodiments, animal byproducts, such as feathers and offal, may be ground by grinding means 66' which may be substantially the same as the grinding means 66. As in the previous non-limiting example embodiments, the animal by products, for example, the feathers and/or offal, may mix with the enzyme digest medium 12' in a closed connection 71' which may be substantially the same as the closed connection 71.

In example embodiments, the at least one prep tank 60', 62' may be a jacketed prep tank that may be heated by injecting steam into the jacket. For example, the at least one prep tank 60', 62' may be a conventional cone bottomed tank. Thus, the at least one prep tank 60', 62' may be heated during the mixing process. For example, the at least one prep tank 60', 62' may be heated such that a temperature of the mixture 84' is heated to about 110° F. or to a range up to about 125° F. or below.

In example embodiments, the at least one prep tank 60', 62' may be a truck mounted or may be part of a fixed structure. Thus, the at least one prep tank 60', 62' may be stationary or mobile.

In example embodiments, after the mixture 84' of the animal product and the enzymatic digest medium 12' has been thoroughly mixed in the at least one prep tank 60', 62' and the animal byproducts have been properly liquefied by the enzymatic digest medium 12', the mixture 84' may be sent to a dryer, for example, a drum dryer, a conveyor dryer, a spray dryer, or a fluid bed dryer, which may be used to dry the mixture 84'.

In example embodiments, when only feathers are used as the animal byproducts, the enzymatic digest medium 12' may only contain keritinase and the enzymatic digest medium 12' may be controlled to have a pH of between about 6 and about 8, for example, about 7. In addition, when only feathers are used as the animal byproducts, the mixture 84' may be thoroughly digested provided it is mixed for a time, for example, greater than about twenty minutes up to about 1½ hours, at a temperature of about 100 F to a temperature at or below about 125 F. Applicants have found that a mixture of one part blood and preservative to about two parts feathers is acceptable for producing a mixture 84' which is thoroughly digested within about an hour. In this particular embodiment, because feathers contain relatively little fat, the mixture 84' may be dried in the dryer without a need to remove fat therefrom.

In example embodiments, the mixture 84' may be stored for a relatively long time. For example, the mixture 84' may be stored for several months. In addition, because the mixture 84' is substantially liquid, the mixture 84' may be pumped from the at least one prep tank 60' and 62' to a holding tank. The holding tank may be a stationary structure. In the alternative, the holding tank may be movable by a truck. Thus, the mixture 84' may be moved from one location to another location. Because the mixture 84' may be moved, a location of a dryer may vary. For example, the dryer may be at a slaughterhouse. In the alternative, the dryer may be located at a site which is remote from the slaughterhouse. In example embodiments, the dryer may be located between slaughterhouses. For example, if a certain region includes two slaughterhouses separated by fifty miles, the dryer may be located between to the two slaughterhouses, for example, twenty five miles from each slaughterhouse.

In example embodiments, when only feathers and offal are used as the animal byproducts, the enzymatic digest medium 12' may contain keritinase, protease, lipase or some combination thereof and may be mixed to have a pH of about 7. In addition, when only feathers and offal are used as the digested protein, the mixture 84' may be thoroughly digested in about fifteen minutes to about one hour provided it is mixed at a temperature of about 110 F to about 120 F and not above about 125 F. Applicants have found that a mixture of one part blood and preservative to about two parts feathers and offal is acceptable for producing the mixture 84' which may be digested within about an hour. In this particular embodiment, because feathers and offal contain relatively little fat, the substantially liquefied mixture 84' may be dried in the dryer without a need to remove fat therefrom, however, the fat may optionally be separated prior to drying the remaining substantially liquefied mixture.

Example embodiments are not limited to treating only feather and offal. For example, the apparatus of example embodiments may also be usable for digesting other animal byproducts such as heads, feet, necks, and backs of birds along with blood and offal or without offal. As in the earlier explained embodiments, at least one of the feet, necks, and backs may be fed into the grinding means 66' and then mixed with the enzymatic digest medium 12' in the at least one prep tank 60' and 62'. For example, the ground heads, feet, neck, and backs may be mixed with the enzymatic digest medium 12' for greater than about twenty minutes (for example, about one hour) at a temperature between 100 F and 120 F and a pH of between about 6 and about 8, for example, about 7. In example embodiments, the enzymatic digest medium 12' may include at least one of lipase, protease, and amylase to digest at least one of the ground heads, feet, neck and backs.

Thus, example embodiments has been described in an illustrative manner. It is to be understood that the terminology that has been used is intended to be in the nature of words of description rather than of limitation.

Many modifications and variations of example embodiments are possible in light of the above teachings. For example, it may be possible for all parts of the system to be made in mobile form or for none of the system to be mobile. Many different pumps are available and may be used according to need. The enzymatic digest medium can be altered to accommodate different protein/bone/feather combinations. Therefore, within the scope of the appended claims, the inventor so defines his invention.

What we claim is:

1. A method of producing a protein byproduct comprising: forming a digest medium comprising at least one enzyme, at least one preservative, and at least one protein source, said digest medium generally biologically stable during storage at ambient temperatures for up to about 30 days; thereafter mixing the digest medium with a plurality of non-hydrolyzed feathers to produce a substantially liquid product; and mixing the substantially liquid product with an absorbing substance.

2. The method of claim 1, wherein said at least one preservative comprises a non-acidifying preservative, and said absorbing substance comprises one or more from a group comprising: cereal, soybean meal, corn, wheat mids, and previously dried material made for such purpose.

3. The method of claim 2, said at least one protein source consisting essentially of animal blood.

4. The method of claim 2, said at least one protein source comprising animal blood and said preservative comprising any one of sodium bisulfite, potassium sorbate, sodium sulfate, and meta-bisulfite.

5. The method of claim 2, said at least one protein source comprising animal blood.

6. The method of claim 2 wherein forming the digest medium further includes monitoring a pH of the digest medium and adjusting the pH of the digest medium by adding at least one pH controlling medium to the digest medium.

7. The method of claim 6, wherein one pH controlling medium comprises an acid and the pH is controlled to about pH 7.

8. The method of claim 7, wherein the acid is phosphoric acid.

9. The method of claim 2, further comprising mixing said digest medium with offal and said at least one enzyme includes keritinase.

10. The method of claim 4, further comprising: controlling a temperature of the substantially liquid product to be about 125 F or below.

11. The method of claim 10, wherein the plurality of non-hydrolyzed feathers and the digest medium are mixed for a time period between about 30 minutes and about 90 minutes to produce the substantially liquid product.

12. The method of claim 11, wherein a pH of the substantially liquid product is about pH 7 and said substantially liquid product exhibits biological stability in storage.

13. The method of claim 9, further comprising mixing the digest medium with at least one animal carcass part selected from the group consisting of: head, neck, wings, back and feet and said at least one enzyme further includes protease.

14. The method of claim 1, further comprising drying the substantially liquid product in one of a drum dryer, a conveyer dryer, a spray dryer, and a fluid bed dryer without removing fat from the substantially liquid product.

15. A method of producing a protein byproduct comprising:
creating a digest medium including blood, at least one enzyme, and a preservative selected from the group consisting of: sodium bisulfate, potassium sorbate, sodium sulfate, and meta-bisulfate, said digest medium comprising biological stability for at least about 30 to about 60 days;
monitoring the pH of the digest medium and adding to the digest medium at least one animal byproduct from the group consisting of: blood, head, feet, neck, back, wings, offal, and feathers;
recirculating the digest medium and said at least one animal byproduct and digesting for a period between about 30 minutes and about 90 minutes at temperature at or below about 125 F until substantially liquid, and mixing the substantially liquid with at least one absorbing substance selected from a group consisting of cereal, soybean meal, corn, and wheat mids.

* * * * *